United States Patent
Haller et al.

(10) Patent No.: US 7,070,577 B1
(45) Date of Patent: Jul. 4, 2006

(54) DRIVE CIRCUIT HAVING IMPROVED ENERGY EFFICIENCY FOR IMPLANTABLE BENEFICIAL AGENT INFUSION OR DELIVERY DEVICE

(75) Inventors: Markus Haller, Begnins (CH); Koen J. Weijand, Rockajne (NL)

(73) Assignee: Medtronic, INC, Minneapolis, MN (US)

( * ) Notice: Subject to any disclaimer, the term of this patent is extended or adjusted under 35 U.S.C. 154(b) by 0 days.

(21) Appl. No.: 09/519,563

(22) Filed: Mar. 6, 2000

Related U.S. Application Data

(63) Continuation-in-part of application No. 09/017,195, filed on Feb. 2, 1998, now abandoned, and a continuation-in-part of application No. 09/494,530, filed on Jan. 31, 2000, now Pat. No. 6,488,652.

(51) Int. Cl.
*A61M 37/00* (2006.01)

(52) U.S. Cl. .................. 604/131; 604/891.1; 604/93.01

(58) Field of Classification Search .................. 604/31, 604/65–67, 93.01, 890.1, 891.1, 131–133, 604/151, 153, 154, 246, 247, 249, 236, 237; 128/DIG. 12, 13; 600/9; 251/129.04, 129.06, 251/129.09, 129.15

See application file for complete search history.

(56) References Cited

U.S. PATENT DOCUMENTS

| | | | | |
|---|---|---|---|---|
| 4,221,219 A | * | 9/1980 | Tucker | 604/141 |
| 4,340,083 A | * | 7/1982 | Cummins | 251/11 |
| 4,443,218 A | * | 4/1984 | DeCant et al. | 604/67 |
| 4,541,429 A | * | 9/1985 | Prosl et al. | 604/249 |
| 4,866,326 A | | 9/1989 | Niikawa et al. | |
| 4,895,500 A | | 1/1990 | Hök et al. | |
| 5,095,256 A | | 3/1992 | Ueyama et al. | |
| 5,096,388 A | | 3/1992 | Weinberg | |
| 5,129,794 A | | 7/1992 | Beatty | |
| 5,147,141 A | | 9/1992 | Sakaida et al. | |
| 5,171,132 A | | 12/1992 | Miyazaki et al. | |
| 5,190,522 A | * | 3/1993 | Wojcicki et al. | 604/65 |
| 5,224,843 A | | 7/1993 | van Lintel | |
| 5,259,737 A | | 11/1993 | Kamisuki et al. | |

(Continued)

FOREIGN PATENT DOCUMENTS

JP 6397854 A 4/1988

(Continued)

OTHER PUBLICATIONS

"Microflow devices and systems"—S. Shoji and M. Esashi (J. Micromech. Microeng. 4 (1994) pp. 157-171).

(Continued)

*Primary Examiner*—Nicholas D. Lucchesi
(74) *Attorney, Agent, or Firm*—Thomas F. Woods; Keith M. Campbell

(57) ABSTRACT

An implantable beneficial agent infusion device featuring a unique energy recovery circuit and a deflectable energy storing member such as a piezo-electric membrane is disclosed. The circuit and deflectable energy storing member cooperate to permit electrical energy employed to activate the member to be at least partially recovered. In a preferred embodiment, the deflectable energy storing member is connected to a seal which is opened to permit the delivery or infusion of a pre-determined amount of a beneficial agent to a patient when the member is deflected or actuated through the application of a sufficiently high voltage thereacross. Charge stored on or in the deflectable energy storing member as a result of the voltage being applied thereacross is recovered by a novel circuit when the deflectable energy storing membrane is permitted to return to its non-actuated state or position.

15 Claims, 8 Drawing Sheets

U.S. PATENT DOCUMENTS

| | | | |
|---|---|---|---|
| 5,328,460 A | * 7/1994 | Lord et al. | 604/67 |
| 5,413,955 A | 5/1995 | Lee et al. | |
| 5,479,062 A | 12/1995 | Yoshino | |
| 5,707,361 A | * 1/1998 | Slettenmark | 604/131 |
| 6,048,328 A | * 4/2000 | Haller et al. | 604/228.03 |
| 6,071,087 A | * 6/2000 | Jalink et al. | 417/322 |
| 6,488,652 B1 | * 12/2002 | Weijand et al. | 604/93.01 |

FOREIGN PATENT DOCUMENTS

| | | |
|---|---|---|
| JP | 2058280 A | 2/1990 |
| JP | 2136245 A | 5/1990 |
| JP | 4309273 A | 10/1992 |
| JP | 4351200 A | 12/1992 |
| JP | 5003683 A | 1/1993 |
| JP | 5344755 A | 12/1993 |
| JP | 6177449 A | 6/1994 |

OTHER PUBLICATIONS

"Piezo drive circuit performance"—C.M. Lopez (Medtronic).

* cited by examiner

DRIVE CIRCUIT HAVING IMPROVED ENERGY EFFICIENCY FOR IMPLANTABLE BENEFICIAL AGENT INFUSION OR DELIVERY DEVICE

RELATED APPLICATION

This patent application is a continuation-in-part of U.S. patent application Ser. No. 09/017,195 to Haller et al. entitled "Implantable Drug Infusion Device Having a Safety Valve Assembly" filed Feb. 2, 1998 now abandoned and is also a continuation-in-part of U.S. patent application Ser. No. 09/494,530 to Haller et al. Entitled "Safety Valve Assembly for Implantable Beneficial Agent Infusion Device" filed Jan. 31, 2000 now U.S. Pat. No. 6,488,652. The disclosures of the foregoing patent applications are hereby incorporated by reference herein, each in its respective entirety.

FIELD OF THE INVENTION

The present invention relates to the field of implantable medical devices, and more particularly to an efficient drive circuit for a safety valve assembly for an implantable beneficial agent infusion device.

BACKGROUND OF THE INVENTION

Implantable drug infusion devices are used to provide patients with a constant and long term dosage or infusion of a drug or any other therapeutic agent. Such devices may be categorized as being active or passive.

Active drug or programmable infusion devices feature a pump or a metering system to deliver the drug into the patient's system. An example of such an active drug infusion device currently available is the Medtronic SynchroMed programmable pump. Such pumps typically include a drug reservoir, a peristaltic pump to pump out the drug from the reservoir, and a catheter port to transport the pumped out drug from the reservoir via the pump to a patient's anatomy. Such devices also typically include a battery to power the pump as well as an electronic module to control the flow rate of the pump. The Medtronic SynchroMed pump further includes an antenna to permit the remote programming of the pump.

Passive drug infusion devices, in contrast, do not feature a pump, but rather rely upon a pressurized drug reservoir to deliver the drug. Thus such devices tend to be both smaller as well as cheaper as compared to active devices. An example of such a device includes the Medtronic IsoMed™. This device delivers the drug into the patient through the force provided by a pressurized reservoir. In particular, this reservoir is pressurized with a drug to between 20–40 psi through a syringe capable of delivering the fluid between 35–55 psi.

Regardless of whether the device is an active or passive drug infusion device, the overriding concern for all drug infusion devices is to ensure patient safety. This includes insuring, among many other things, that only the exact intended amount of drug is delivered to the patient. Thus, one drawback to active devices which feature pumps that are not normally closed, such as those disclosed in U.S. Pat. Nos. 5,277,556; 5,224,843 and 5,219,278 is that in the vent the device malfunctions or changes occur in the fluid pathway, then more drug than intended may reach the patient. Similar risks are inherent in passive devices which, should the flow regulator fail or the pressure reservoir be over pressurized, may lead to more drug than intended to reach the patient.

Yet another problem concerning prior art implantable drug or beneficial agent medical devices is the amount of electrical power which they consume. Implantable medical devices are usually powered by a single primary, non-rechargeable battery. Excessive power consumption in an implantable medical device is highly undesirable because the only remedy for low state of charge in the battery of such a device is battery replacement or device replacement (which generally requires explantation of the device).

Thus there exists a need for an implantable drug infusion or delivery system which features a means of prolonging battery life and maintaining an acceptable state of charge therein.

SUMMARY OF THE INVENTION

The present invention is an implantable beneficial agent or drug infusion or delivery device which features a unique energy conservation circuit and method. In one embodiment of the present invention, the safety valve assembly comprises a piezo-electric membrane and a corresponding seal mechanically openable in response to actuation of the membrane, where the seal is placed into an open position only upon the membrane being actuated, deflected or moved through the application of a sufficient voltage across the membrane. Voltage and charge developed across and in the membrane to actuate same are recovered by a circuit of the present invention when the membrane is permitted to return to its initial, un-actuated position. The piezo-electric membrane and energy conservation circuit of the present invention may be employed in either a passive or an active drug or beneficial agent implantable infusion or delivery system.

The Figures are not necessarily to scale.

DETAILED DESCRIPTION OF THE PREFERRED EMBODIMENTS

This patent application hereby incorporates by reference into the specification hereof each of the following patent applications, each in its respective entirety: (1) U.S. patent application Ser. No. 09/239,306 to Haller et al. entitled "System for Locating Implantable Medical Device"; (2) U.S. patent application Ser. No. 09/014,196 to Haller et al.

entitled "Implantable Drug Infusion Device Having a Flow Regulator"; and (3) U.S. patent application Ser. No. 09/017,194 to Haller et al. entitled Implantable Drug Infusion Device Having an Improved Valve".

Figure 1:
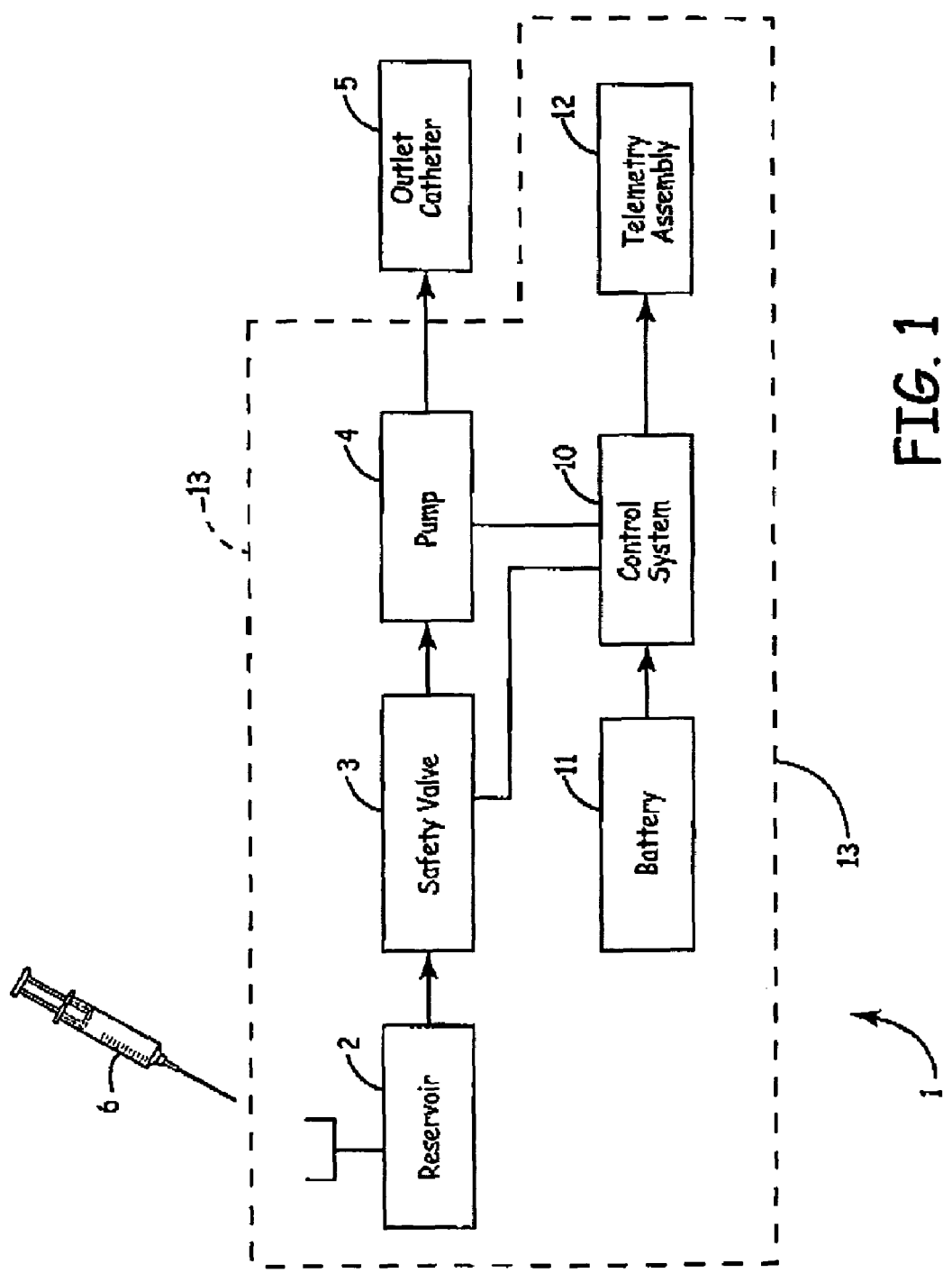
FIG. 1 is a block diagram of the present invention.

FIG. 1 shows a block diagram of the present invention. As seen, such a system 1 comprises a reservoir 2, safety valve assembly 3 assembly, pump 4, electronic controls 10, battery 11, telemetry assembly 12 and outlet catheter 5. Outlet catheter may be of any model desired and suited to the patient's requirements. Safety valve 3 assembly is coupled to the reservoir and also to pump 4. Pump may be of any suitable design, including a roller-type pump as found in the SynchroMed™ or a micro-machined pump, for example. Pump 4 is coupled, in turn to outlet catheter 5, such that fluid form reservoir 2 may be pumped through safety valve assembly and out to outlet catheter. Pump is controlled by electronic controls 10. These controls include, among other devices, an efficient circuit to drive the membranes used in safety valve assembly 3. The device may be refilled through injection port 5 through the use of a needle 6 as is well known. This refill procedure may be further enhanced through the use of the system as described in the above-referenced '306 patent application to Haller. Surrounding all components of the implantable pump other than the outlet catheter is a hermetic closure 13 as is well known in the art. The device may further feature, if desired, a flow regulator, such as that shown in the '196 patent application to Haller.

Figure 2A:
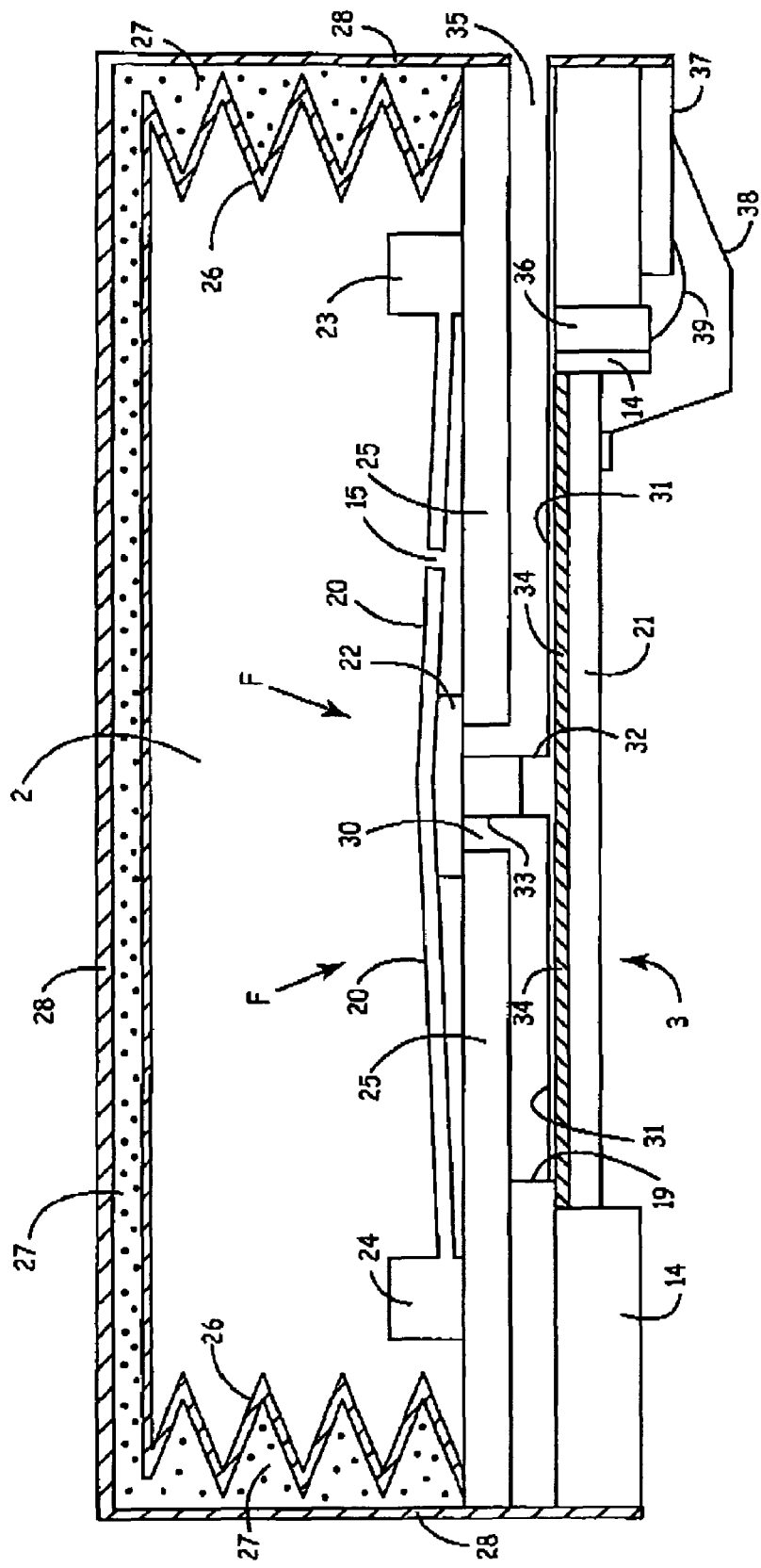
FIG. 2A is a side view of one embodiment of a safety valve assembly of the present invention in a closed position.

FIG. 2A shows a cross-sectional view of one embodiment of safety valve assembly 3 of the present invention in the closed position. Hermetically sealed collapsible reservoir 2 is filled with a desired beneficial agent, drug, medicament, or pharmaceutical such as by needle refilling through a reservoir fill port and self-sealing septum know in the art. Examples of the beneficial agents, drugs, medicaments, and pharmaceuticals that may be infused into a patient's body with the device and method of the present invention include, but are not limited to, gene therapeutic agents, protein- or peptide-based drugs, morphine, BACLOFEN®, antibiotics, and nerve growth factors.

Bellows 26 form the sidewalls of reservoir 2, and are preferably formed from titanium in a manner similar to that employed to form the titanium bellows employed, for example, in the MEDTRONIC® SYNCHROMED® infusion system. Of course, materials other than titanium may be employed to form bellows 26. When formed of titanium, bellows 27 are most preferably about 50 microns to about 75 microns thick.

Propellant 27 is disposed in the volume existing between the outwardly-facing walls of bellows 26 and the inwardly-facing walls of outer walls 28 (within which most of safety valve assembly 3 is disposed). An appropriate formulation of bi-phasic fluorocarbon may be employed as propellant 27, and may be obtained from 3M Corporation in St. Paul, Minn. Propellant 27 is intended to cause a relatively constant pressure to be exerted against the outwardly-facing walls of bellows 26 when held at a temperature at or near human body temperature (e.g., 35–39 degrees Celsius).

Safety valve assembly 3 further includes deflectable upper member or membrane 20, seal 22 mounted on or attached to intermediate member or cap 33/34, first substrate 25, second substrate 14, deflectable or moveable lower member 21, and shoulder 19. Upper membrane 20 is preferably formed of titanium metal and has a thickness ranging between about 25 microns and about 50 microns, but may be thicker (e.g., up to 100 microns) or thinner (e.g., 20 microns). Upper membrane 20 may alternatively be formed of silicone, in which case its thickness would range between about 10 microns and about 20 microns. Upper membrane 20 is preferably about 6 to about 15 mm in diameter. Seal 22 most preferably forms an o-ring structure and comprises a deformable material such as silicone rubber, polyimide, TEFLON (PTFE or polytetranfluoroethylene), a polymeric substance, or any other suitable material. Seal 22 preferably has a diameter ranging between about 1 and 3 mm, or between about 25 and about 50 microns. Shoulder 19 may be formed of titanium, silicon, or any other suitable material.

Depending on the composition of shoulders 23/24 and first substrate 25, shoulders 23/24 may be attached to substrate 25 by connecting means such as brazing, welding, anodic bonding, or silicon fusion bonding, such means being selected on the basis of the materials forming shoulders 23/24 and first substrate 25. Cap 32/33 is most preferably about 1 mm in height, about one-half the diameter of seal 22 (e.g., between about 0.5 mm and about 1.5 mm), and most preferably comprises nipple 32 formed of silicon, silicone rubber, or titanium or any other suitable material, and end cap 33 formed of glass, silicon, silicone rubber, or titanium or any other suitable material. The height of intermediate member or cap 32/33 is preferably determined by the thicknesses of first substrate 25 and shoulder 19. Cap 32/33 may be glued or otherwise attached to member 31, or alternatively may form a single piece or component in respect of member 31 or lower member 21.

Fluid in reservoir 2 exerts a pressure or force F on the top surface of membrane 20, thereby pushing membrane 20 down, onto and against the upper surface of seal 22. To aid in preventing the undesired opening of safety valve assembly 3, it is preferred that membrane 20, connecting shoulders 23 and 24, seal 22, cap 32/33, and deflectable or moveable lower member 21 be configured and cooperate with one another such that membrane 20 is under mechanical tension and stretched over seal 22, even in the absence of force or pressure provided by fluid disposed in reservoir 2.

The ends of membrane 20 are attached to shoulders 23 and 24 by any of a number of known connecting means such as brazing, welding, anodic bonding, or silicon fusion bonding, such means being selected on the basis of the materials forming upper membrane 20 and shoulders 23 and 24. In the closed position of safety valve assembly 3, the lower surface of seal 22 is pushed down against substrate 25 by upper membrane 20. Cap 32/33 may be formed of two portions, nipple 33 and end cap 34, or may comprise a single portion. The upper surface of cap 32/33 is attached to seal 22, while the lower surface of cap 32/33 is attached to, the upper surface of member 31. Connecting member 31, in turn, is preferably attached to deflectable or moveable lower member 21 by electrically conductive epoxy 34 or other suitable means.

The ends of connecting member 31 are attached to substrate 14 by any of a number of known connecting means such as brazing, welding, anodic bonding, or silicon fusion bonding, such means being selected on the basis of the materials forming connecting member 31. Alternatively, connecting member 31 may form a single contiguous piece of material extending laterally away from the edges or perimeter of lower member 21. The upper surface of lower member 21 is preferably attached to connecting member 31 by means of electrically conductive epoxy, the ends of lower member 21 not being attached to second substrate 14. Deflectable or moveable lower member 21 is most preferably formed from a suitable piezo-electric or piezo-crystal material such as PZT (lead zirconium titanate) or PMN (lead magnesium niobate). A piezo-electric material is preferred for deflectable or moveable member 21 because piezo-electric materials are capable of undergoing relatively large displacements when subjected to an electric field. Other embodiments of lower member 21 are contemplated in the present invention, however, such as electrostatic, electro-capacitive and solenoid embodiments of lower member 21, where motion and displacement are imparted to member 21 by means of electric or magnetic fields, or the flow of electrical current.

Integrated circuit 37 is shown as being disposed on the underside of second substrate 14, and preferably receives electrical power from a battery (not shown in FIG. 2A). Integrated circuit 37 comprises a driving circuit, which receives electrical power from a battery or other power source and transforms it into a signal appropriate to cause lower member 21 to move upwardly in response to the application of an electrical filed. It is preferred that integrated circuit 37 provide an output voltage ranging between about +80 and +150 Volts. Wire bonds 38 and 39 provide the electrical connections required to permit such an output voltage to be applied across the top and bottom surfaces of lower member 21. Other electrical connection techniques may be employed than wire bonds to provide the output signal to the lower member including, but not limited to, flextape, solder and the like. Wire bond 39 is most preferably held at ground and electrically connected to electrically conductive epoxy 34 via an electrical connector in feedthrough 36 disposed in second substrate 14. Alternatively, the top end of the electrical connector in feedthrough 36 may be electrically connected to another type of electrically conductive coating or member disposed on the upper surface of deflectable or moveable lower member 21, such as an evaporated, vacuum deposited, electrochemically plated or other electrically conductive plating or member. Wire bond 38 is most preferably switched to a voltage ranging between about +80 and +150 Volts when it is desired to move lower member 21 and seal 22 into the open position.

Figure 2B:
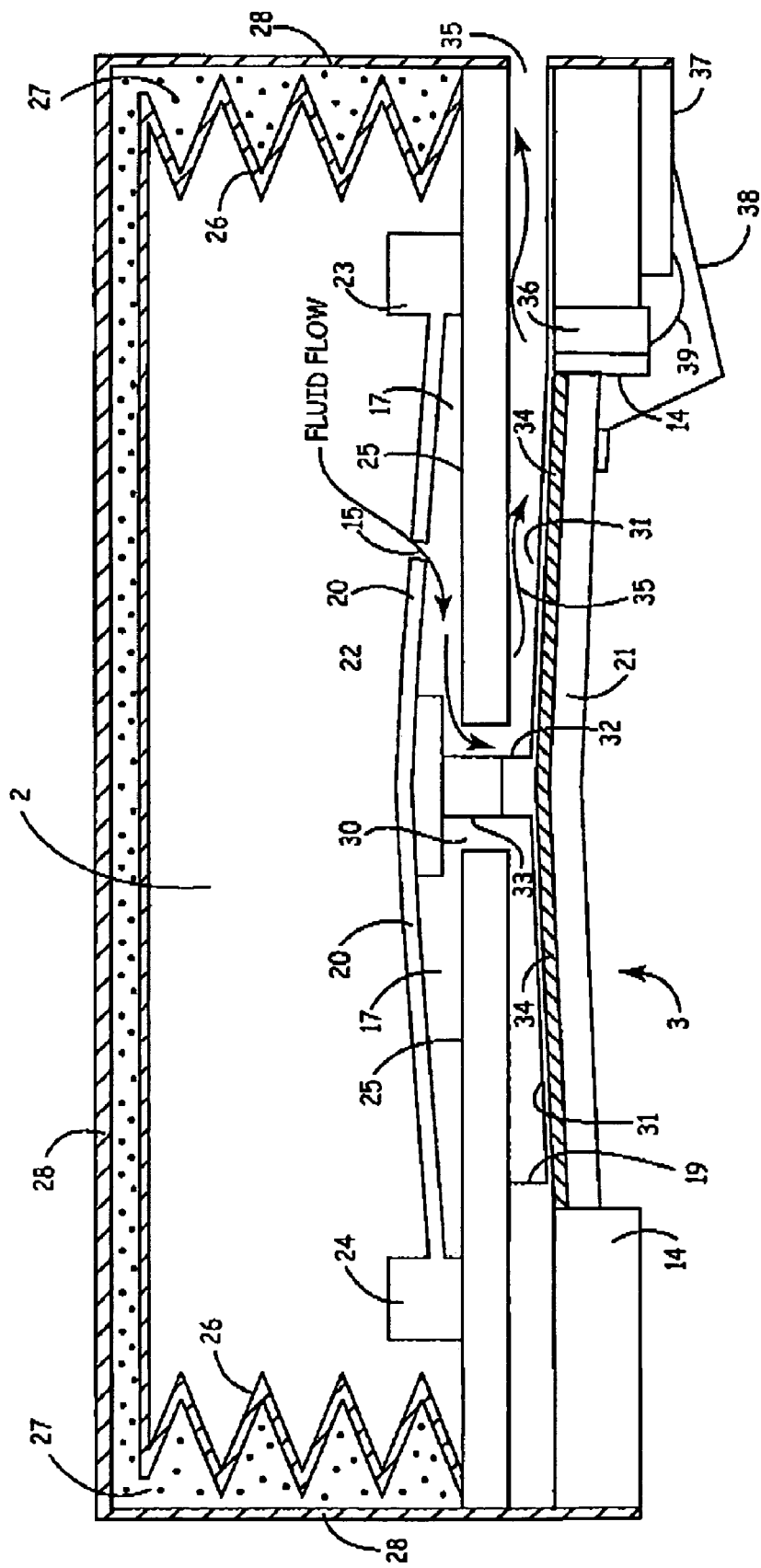
FIG. 2B shows the safety valve assembly of FIG. 2B in an open position, thereby permitting fluid egress from the reservoir thereof.

FIG. 2B shows the safety valve assembly of FIG. 2A in the open position, where deflectable or moveable member 21 has moved upwardly in response to an electrical voltage being applied thereacross by integrated circuit 37. Seal 22, the underside of which is connected to lower member 21 via cap 32/33, member 31 and glue 34, has moved upwardly such that the top surface thereof has engaged and pushed up against the underside of membrane 20 to cause membrane 20 to be deflected upwardly. Fluid present in reservoir 2 and residing in intermediate volume 17 (after having passed through membrane passageway 15) now flows into exit passageway 35 for eventual delivery to the patient. Via catheter and pump means (not shown). Once the voltage applied across lower member 21 is withdrawn, lower member 21 returns to the position illustrated in FIG. 2A and further delivery of the fluid contained in reservoir 2 is terminated.

It is an advantage of the present invention that safety valve assembly 3 is maintained in the closed position when power is withdrawn or lost from the implantable medical device within which it is disposed (e.g., the battery thereof becoming depleted below a certain voltage, etc.), when reservoir 2 is overfilled during refilling, or when external factors such as changes in temperature or pressure occur such that reservoir 2 becomes overpressurized.

The various components of safety valve assembly 3 (e.g., member or membrane 20, seal 22, lower member 21, cap 32/33, etc.) may be configured mechanically such that seal 22 cannot be pushed into the open position, and lower member 21 cannot move upwardly sufficiently to cause seal 22 to open, when a nominal output voltage is applied across lower member 21 and when reservoir 2 has been overfilled to the point of excessive fluid pressures having developed within reservoir 2. That is, the various components of safety valve assembly 3 may be configured such that seal 22 can move into the open position only so long as the pressure or force applied to the upper surface thereof by the fluid contained in reservoir 2 does not exceed a predetermined amount or limit. Such a design prevents the inadvertent and unintended delivery of excessive amounts of the drug contained within reservoir 2 to the patient.

It is contemplated in the present invention that the specific configuration of upper member 20, lower member 21, and seal 22 presented in the drawings hereof be modified such that upper membrane 20 is deflected in response to the provision of an output signal thereto while lower membrane 21 and seal 22 remain in relatively fixed positions.

Figure 3A:
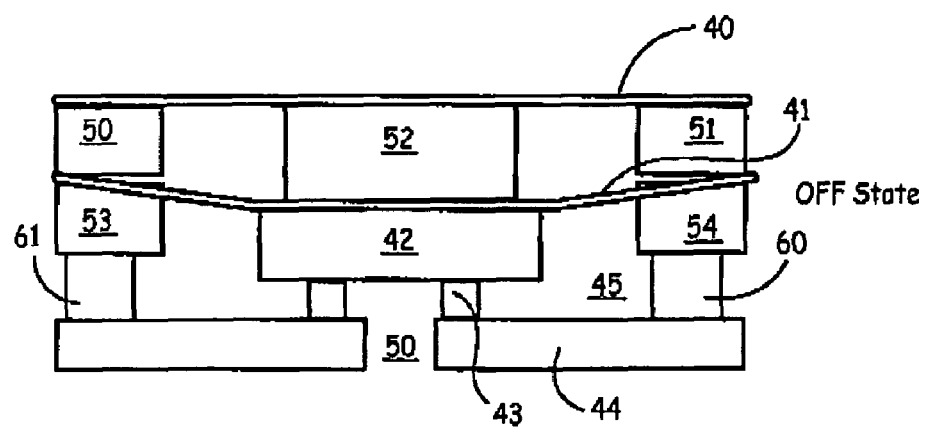
FIGS. 3A and 3B disclose an alternative embodiment of the safety valve assembly of the present invention.
Figure 3B:
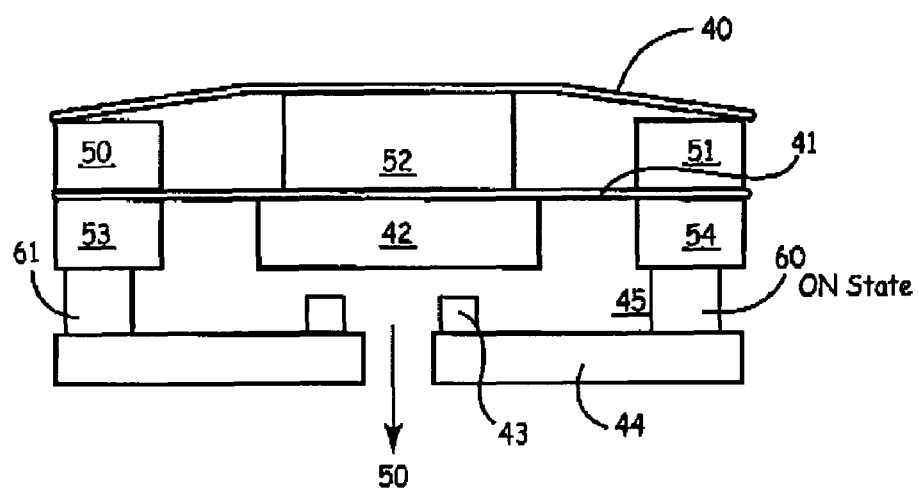

FIGS. 3A and 3B disclose an alternative embodiment of the safety valve assembly of the present invention. Such an embodiment features shape memory alloy membranes as opposed to the piezo-electric membranes disclosed above. This embodiment features a superior membrane 40 and an inferior membrane 41. Membrane 40 is biased in an upward direction while membrane 41 is biased in a downward direction. The respective biasing strengths of these membranes control membrane 40 to normally close the valve when no energy is provided to membrane 41. Upon energizing the membrane 41, however, the shape memory alloy undergoes a reorganization of the crystalline structure. As constructed, this removes the bias to membrane 41. Membrane 40 will, in turn, overcome the bias provided by membrane 41 and thus move the seal assembly 42 upwardly and away from seal footing 43 mounted on substrate 44 thereby creating a fluid passage from cavity 45 to passageway 50. As seen, membrane 40 is mounted across shoulder elements 50 and 51 and includes center portion 52. The shoulder and center portions are preferably constructed of glass. As further seen, membrane 41 is disposed on the downward surface of shoulder and center portion and further mounted to bases 53 and 54. Bases as well as seal assembly 42 are also constructed from glass. This entire assembly is further mounted to substrate 44 through contacts 60 and 61. Contacts 60 and 61 are preferably constructed from silicone. Substrate 44 is preferably constructed of glass while footing 43 is constructed of silicone. Membranes are preferably constructed from Nitinol, although other shape memory alloys may also be used. Moreover, the areas of substrate and membranes in contact with any drug or fluid are further preferably coated with diamond or diamond-like carbon so as to inhibit any interactions between the drug or fluid and the materials. Such coatings may be selected according to the particular drug or fluid to be infused, and may include also tantalum or titanium, for example.

The operation of this embodiment may be seen in FIGS. 3A and 3B. At rest, or when no energy is provided to membranes, the particular bias to membranes causes seal assembly 42 to snugly engage against footing 43. Once energy is provided to the membranes, the energy or electric current causes the material to heat up and thereby ending the phased transformation, i.e., the crystalline structure is reorganized. Thus seal assembly 42 is caused to disengage against footing 43 and thereby opens a fluid pathway from cavity 45 into passageway 50. Of course, although in this embodiment a double membrane design is shown, other embodiments may feature a single, biased membrane as well as three or more membranes, depending upon the exact fluid pathway required.

One problem concerning implantable drug or beneficial agent medical devices is the amount of electrical power which they consume. Implantable medical devices are usually powered by a single primary, non-rechargeable battery. Excessive power consumption in an implantable medical device is highly undesirable because the only remedy for low state of charge in the battery of such a device is battery replacement or device replacement (which generally requires explantation of the device).

Another problem associated with prior art piezo-electric membranes is that known driver circuits typically dissipate the charge built up after a voltage was applied across the membrane, resulting in a waste of the built-up charge. One feature of the present invention is the use of a driver circuit which minimizes the energy consumed in actuating piezo-electric membranes or other suitable deflectable means for storing electrical energy. The present invention provides a driver circuit for collecting the energy stored in a piezo-electric membrane or other suitable deflectable means for storing electrical energy when the voltage on the membrane or means is switched to zero.

Figure 4:
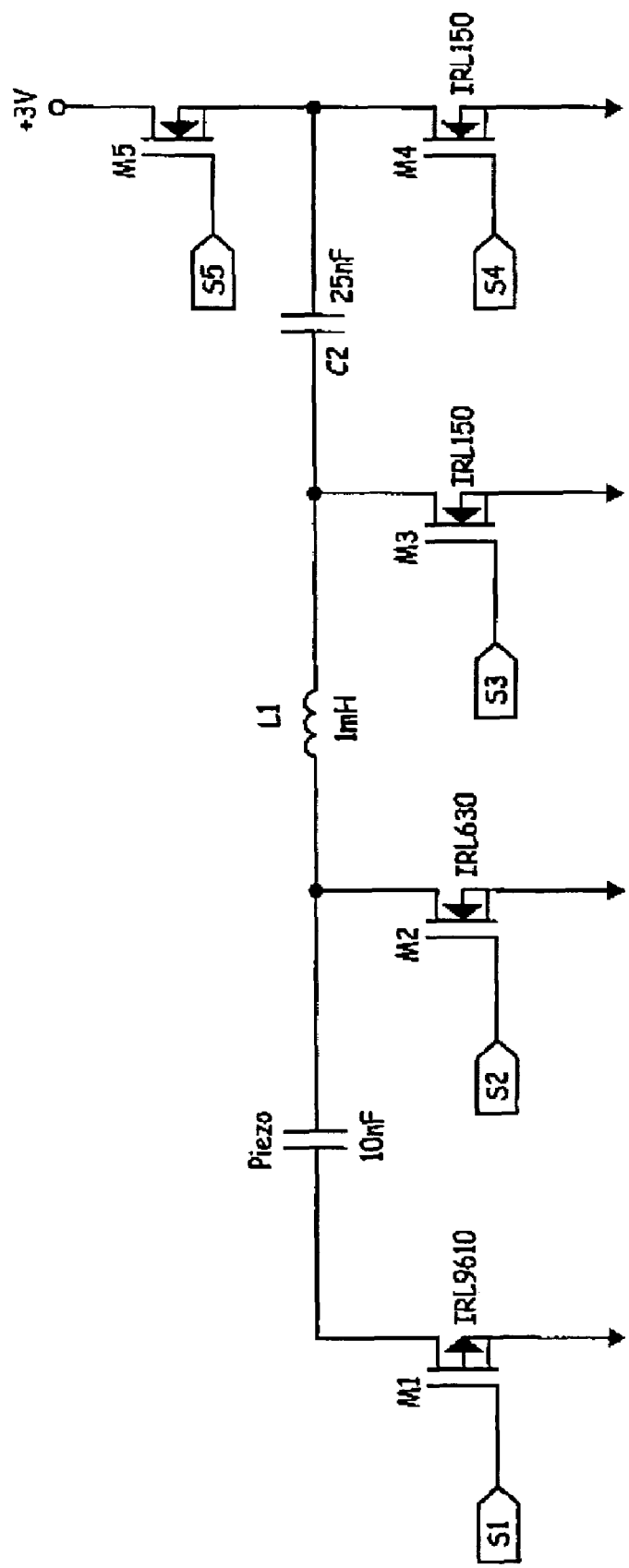
FIG. 4 is a schematic diagram of one embodiment of a driver circuit employed to control a piezo-electric embodiment of the lower member shown in FIGS. 2A and 2B which recovers energy stored on a piezo-electric substrate when the voltage on the piezo-electric member is switched off.
Figure 5:
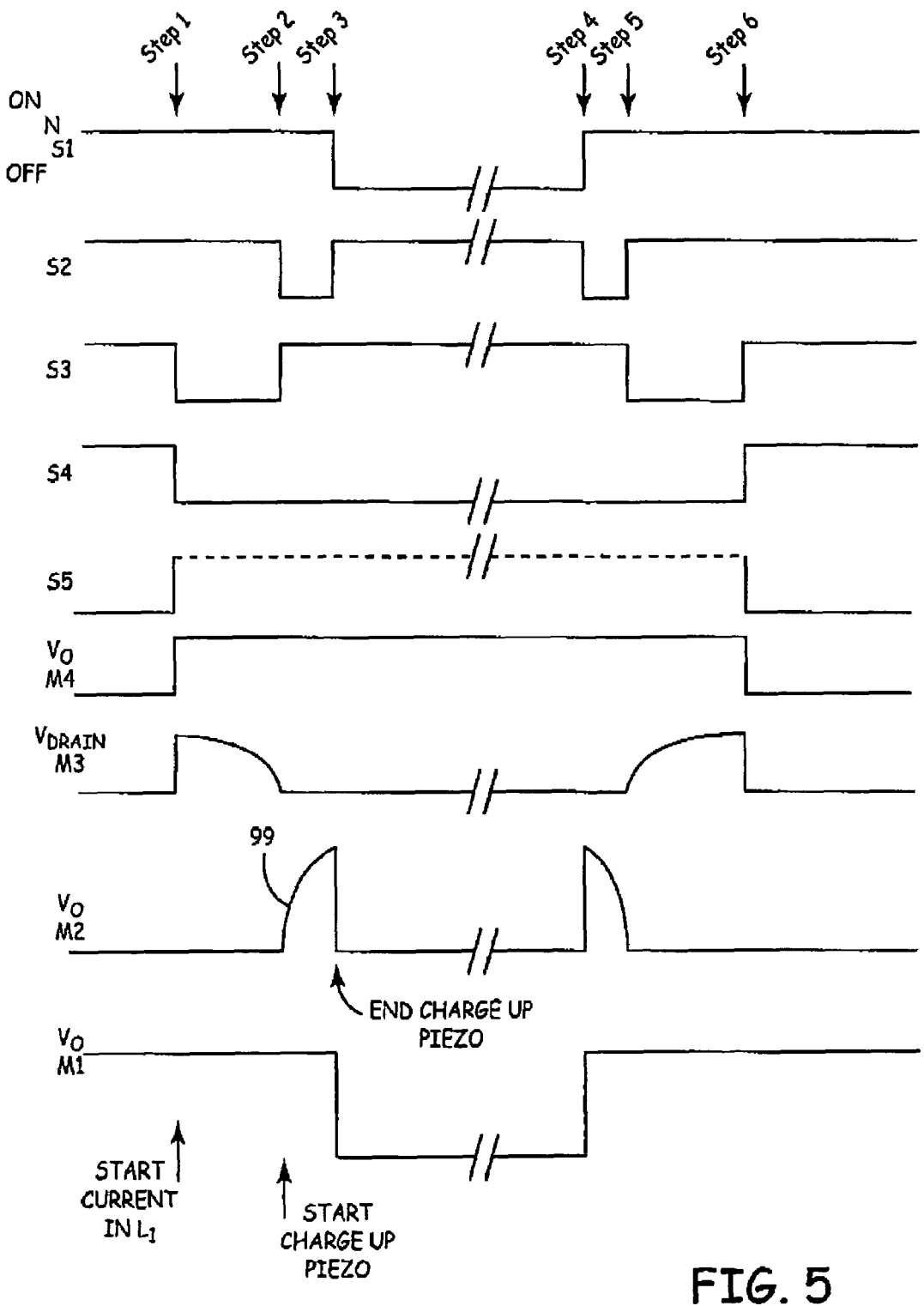
FIG. 5 is a timing diagram of the operation of the driver circuit shown in FIG. 4.

FIG. 4 shows a schematic diagram of one driver circuit used to control the piezo-electric membrane shown in FIGS. 2A and 2B. The circuit recollects electrical energy stored in the piezo-electric membrane when the voltage applied across the piezo-electric membrane is switched to zero. FIG. 5 is a timing diagram of the operation of the driver circuit shown in FIG. 4. The circuit consists of a 3V power supply, four NMOS transistors with low resistance, 1 PMOS transistor, a storage capacitor, an inductor and a piezo-electric membrane. Switches M1 and M2 are high voltage devices. Switches M3–M5 are low voltage devices. In its initial state, all switches but switch M5 are closed.

In step 1 (with reference now also to FIG. 5) switches M3 and M4 are opened and switch M5 is closed to thereby charge capacitor C2 through inductor L1. In step 2, switch M2 is opened and switch M3 is closed, thereby connecting inductor L1 to the piezo-electric membrane. The current in inductor L1 is maintained while a voltage is developed across switch M2 (as best illustrated by line 99 in FIG. 5), resulting in a voltage developing across the piezo-electric membrane. Once the voltage across the piezo-electric membrane and L1 reaches a maximum, step 3 begins. Switch M1 is opened and switch M2 is closed, thereby shorting inductor L1 and maintaining the voltage across the piezo-electric membrane. The voltage actuates the piezo-electric membrane and may be maintained thereacross so long as actuation thereof is desired.

In steps 4, 5 and 6 the above-described process is reversed. In step 4, switch M2 is opened and switch M1 is closed, thereby discharging the voltage across the peizo-electric membrane through inductor L1. In step 5, switch M3 is opened and switch M2 is closed. Current flows through inductor L1 to capacitor C2, thereby discharging C2. Finally in step 6, M5 is opened and M3 and M4 are closed, thereby returning the circuit to its initial state. In such a manner the piezo-electric membrane may be actuated while consuming a minimum amount of energy. The amount of energy delivered to the piezo-electric element is determined by the amount of energy delivered to inductor L1, which in turn is determined by the amount of time elapsing between step 1 and step 2. If capacitor C1 is not completely charged, then operation of the circuit changes slightly (i.e., in step 2 switch M5 opens, switch M4 opens, and switch M3 closes). Thereafter operation of the circuit remains as described above (although in step 5 switch M5 is closed). Additional functionality to monitor voltage and/or current, or to determine the proper timing for closing the switches is not shown explicitly in the Figures, but is performed in block 10 of FIG. 1.

Figure 6:
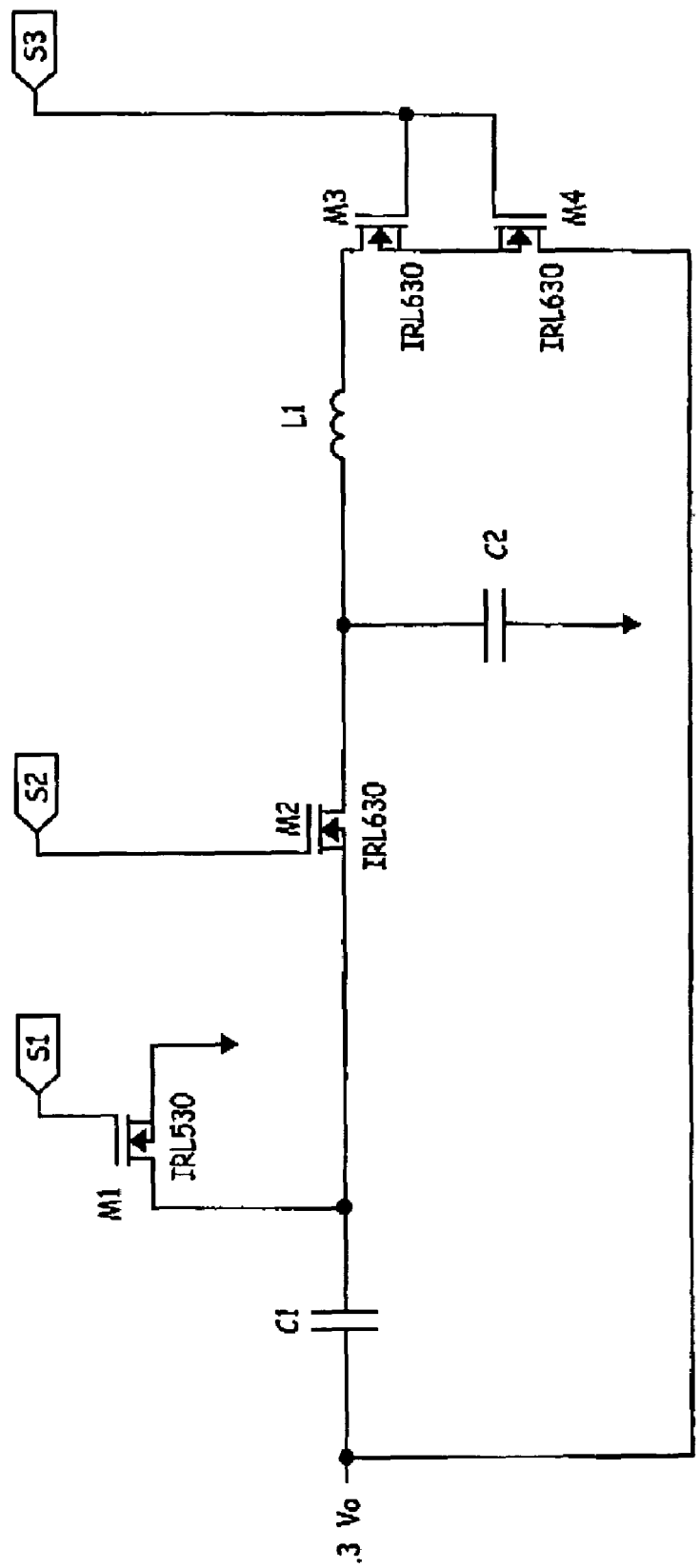
FIG. 6 depicts an alternative driver circuit for a piezo-electric member.
Figure 7:
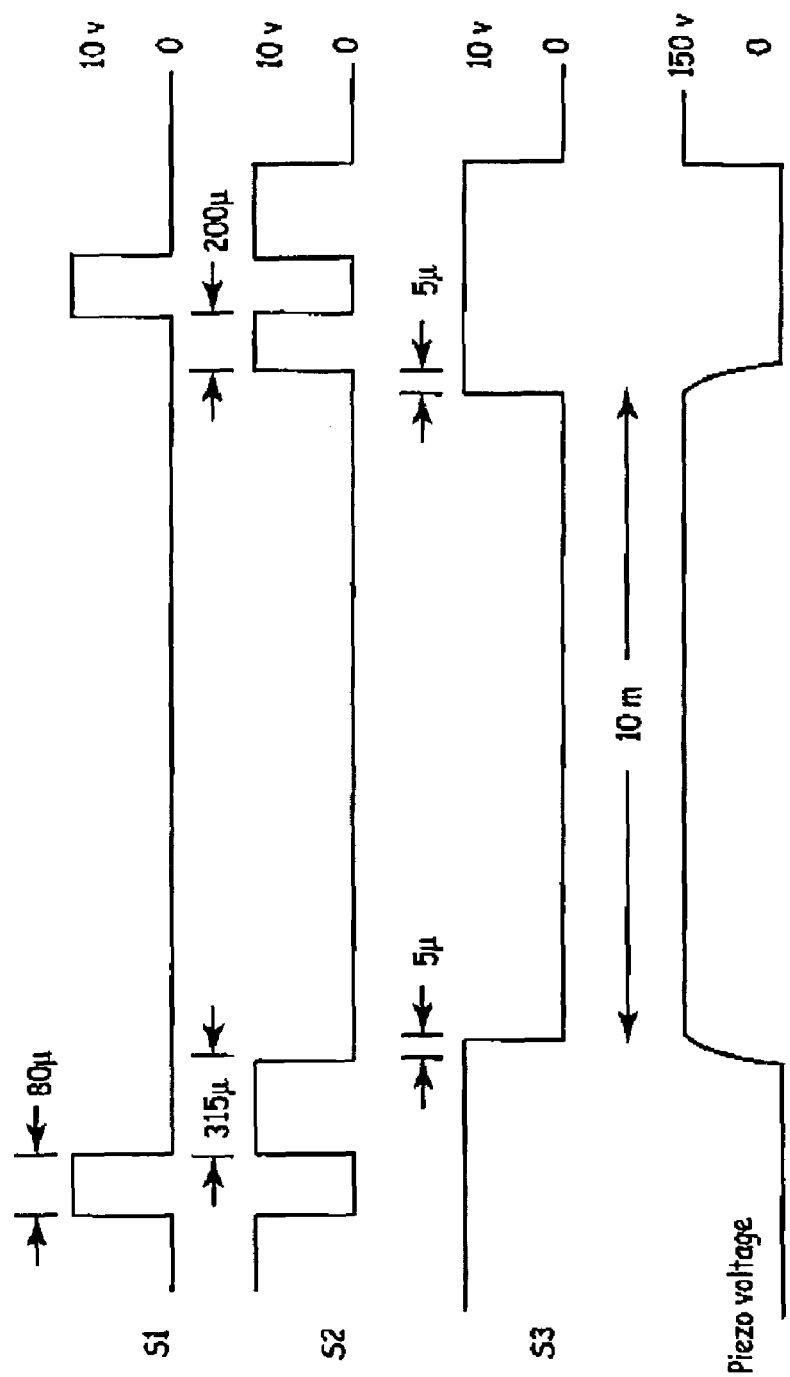
FIG. 7 is a timing diagram of the circuit shown in FIG. 6.

FIG. 6 depicts an alternative embodiment of the driver circuit of the present invention. FIG. 7 is a timing diagram of the circuit shown in FIG. 6. The overall function of this drive circuit is to produce a 150V pulse across the piezo-electric membrane through the storage and transfer of energy from a power supply to capacitors and an inductor. The overall circuit can be broken down into two functional blocks, the energy transfer circuit and the pulse generation circuit.

The main purpose of the energy transfer circuit is to perform the transferring of energy between components to achieve the 150 V pulse across the piezo-electric membrane. The full schematic for the energy transfer circuit is shown in FIG. 6. This circuit consists of a three volt power supply, storage capacitor C1, a piezo-electric membrane (modelled in FIG. 6 as capacitor C2), inductor L1, and four NMOS switches M1 through M4. Pulses S1 through S3 in FIG. 7 are 10 Volt square wave pulses created by the pulse generation circuit.

The first step in creating the pulse for driving or actuating the piezo-electric membrane is to charge storage capacitor C1 to the voltage level of the power supply by closing switches M1 and M3/M4. After C1 is fully charged to the supply voltage, inductor L1 is charged with current by discharging energy stored in capacitor C1. This is done by simultaneously opening M1 while closing M2 and keeping M3/M4 closed. Then M2 is reopened while M3/M4 remains closed to charge piezo-electric membrane C2 with the stored current. The voltage on C2 rises to 150V and all switches are opened while the pulse remains high.

After the pulse has been applied to piezo-electric membrane, switches M3/M4 are closed to drain the energy from the piezo-electric membrane into inductor L1. After the charge on the piezo-electric membrane has been drained, switch M2 is closed while switches M3/M4 remain closed to charge capacitor C2 with the energy stored in the inductor L1. The cycle begins again with another rising edge on switch M1. The timing diagram of FIG. 7 illustrates the timing sequence for closing of switches M1, M2, and M3/M4, where time units are in seconds.

The theoretical oscillating frequency between an inductor and capacitor is determined by the expression:

$$f = \frac{1}{2\pi \cdot \sqrt{L \cdot C}}$$

where f is the oscillating frequency, and L and C are the inductance and capacitance values. The peak current flowing into the inductor occurs at for ¼ of the period, T, which is the inverse of the oscillating frequency. Therefore, a maximum amount of current can be stored in inductor L1 by draining C1 for approximately 315 μs when M2 and M3/M4 are closed. The second pulse of S2 which charges C1 back up is only 200 micro-seconds due to energy dissipation from resistive losses. In similar fashion, the 10 nF piezo-electric membrane can be charged to a maximum voltage if switch M3/M4 is only closed until peak current is reached between the piezo-electric membrane and the inductor. Accordingly, switch M3/M4 is closed for 5 micro-seconds and then reopened as the voltage across the piezo-electric membrane rises to 150 V (and is maintained by the capacitance of the peizo-electric membrane).

The amount of energy stored in a capacitor is defined by the following expression:

$$E = \frac{V^2 \cdot C}{2}$$

where E represents the energy in joules, V is the voltage applied in volts, and C is the capacitance in farads. To determine the size of the storage capacitor, first the energy needed for a 150 V pulse across the 10 nF piezo-electric membrane is calculated to be 112.5 µJ. This amount of energy must be stored in storage capacitor C1 and the input voltage of the power supply is known to be 3 V. The appropriate capacitance for C1 to store the necessary 112.5 µJ is therefore 25 µF. Due to energy losses from the resistance of the NMOS switches, a 150 V pulse cannot be achieved with a 25 µF capacitor. Thus, a 47 µF capacitor is better suited for C1.

The square wave timing signals for the circuit shown in FIG. 6 may be implemented using a National Instruments PC-TIO counter card in conjunction with Labview software. The output timing signals from the PC-TIO are then level shifted to a 10 V output using NMOS switches along with NOR gates. The schematic shown in FIG. 8 depicts the overall timing circuit where T1–T5 represent the outputs from the five separate timers on PC-TIO card.

The use of Labview software was utilized to program the delay, pulse width, triggering, and polarity of each timer used. Five separate counter/timers on PC-TIO were utilized to create the three driving signals, S1–S3. The first timer output of the PC-TIO card, T1, is simply a 90 Hz pulse train with a duty cycle adjusted to create a 80 us pulse for signal S1. The first pulse of 315 µs on signal S2 is created using the output of the second timer, T2, where it is triggered on the rising edge of T1 and delayed 80 µs while C1 is charging. The second pulse of 200 µs pulse on S2 is created using the output of the third timer, T3, and is triggered off the falling edge of T2 and is delayed for 10.02 ms while the piezo is high. The use of the NOR gate, with the outputs of the second and third timers as its input, creates one S2 signal with two pulses. The creation of S3 is done using a similar method where the output of the fourth timer, T4, is the first 395 µs pulse on S3 and is triggered off the rising edge of T1. The second 205 µs pulse on S3 is created from the fifth timer output, T5, and is triggered on the falling edge of T4 and delayed for 10 ms while the piezo is at 150 V.

The drive circuit was successful in creating a 150 V pulse across a 10 nF piezo-modeled capacitor. However, the leakage current in the N-MOS switch M2 prevents the pulse from having a stable voltage while the piezo is "high". Over the period of the 10 ms pulse, the voltage drifted from its initial 150 V down to approximately 125 V. The pulse also has an initial overshoot of approximately 6 V.

Voltage oscillations were observed on the piezo capacitor during the beginning of each cycle when C2 is being charged. This occurs due to the short-circuiting of the power supply which happens as switch M1 is closed. The small resistance of 0.4 ohms of the transistor provides a heavy load and causes the power supply to surge down. This "dip" in power supply voltage is seen as a pulse to the inductor and piezo where oscillations are amplified by the "Q" factor between them. A stable power supply capable of handling heavy loading is necessary to avoid these oscillations.

Improvements in the efficiency of the drive circuits presented herein are desirable. The total energy stored within the C1 is approximately 211.5 µJ, while the energy needed to charge the 10 nF piezo is only 112.5 µJ which translates into approximately 50% efficiency. The majority of the losses occur in the energy dissipation within NMOS switch resistances in M2, M3, and M4 while the inductor is being charged. During the 315 µs when the 1 mH inductor is charging the peak current is approximately 0.3 A. The three NMOS switches (each having a resistance of 0.4 ohms) used during charging dissipate 113.4 µJ, thereby reducing the efficiency of the drive circuit. Improving the efficiency of the circuit can be accomplished in two ways: reduce the amount of time to charge the inductor with current or reduce resistances during current charging.

Reducing the amount of time needed to charge the inductor can be done by lowering the inductance of L1. Lowering the inductance of L1 will increase the oscillating frequency between L1 and C1, or decrease the period. Therefore, the amount of time to reach peak current is reduced. However, increasing the oscillating frequency results in a faster clock speed in the timer card being required. The choice for the 1 mH inductor was made to accommodate the limitations in clock speed of the PC-TIO card where its clock period can be changed in increments of 1 µs.

Another option to increase circuit efficiency is to reorganize the energy transfer circuit to minimize resistive losses. The schematic shown in FIG. 5 depicts one circuit design which so limits resistive losses. The circuit shown in FIG. 5 uses only two FETs, one PMOS and one NMOS having switch resistances of about 0.4 ohms while the remaining FET switches have resistances in the range of 50 milliohms. During the charging of current into the inductor from C2 only one high voltage FET (M2) is employed, thereby minimizing resistive losses. The increase in number of switches within the circuit adds more complexity to the timing structure required.

Although specific embodiments of the present invention are disclosed herein, this is done for purposes of illustration only and is not intended to be limiting with regard to the scope of the invention. It is contemplated various substitutions, alterations and/or modifications may be made to the disclosed embodiment without departing from the spirit and scope of the invention. Such modifications may include substituting elements or components which perform substantially the same function in substantially the same way to achieve substantially the same result as those described explicitly herein. For example, the scope of the present invention is not limited to circuits or devices where charge recovered from the piezo-electric membrane is maintained in a storage capacitor for later use in actuating the membrane. Instead, the present invention includes within its scope embodiments where the charge recovered from the membrane is employed to re-charge the power source (e.g., battery or super-capacitor providing power to the charge recovery and/or membrane actuation circuits). Additionally, the power source employed in conjunction with the circuit of the present invention need not be a single electrochemical cell or battery, but may be a capacitor, electrolytic capacitor or a super-capacitor. Moreover, the energy storing member of the present invention from which electric charge is recovered for later use is not limited to piezo-electric membranes or materials, but instead includes within its scope electro-capacitive materials and members, electro-static materials and members, solenoids, and other suitable materials, members and devices.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

All patents and printed publication referenced hereinabove are hereby incorporated by reference herein, each in its respective entirety.

What is claimed is:

1. An implantable beneficial agent infusion device, comprising:
   an hermetically sealed enclosure;
   a fluid reservoir positioned at least partially within the hermetic enclosure, the fluid reservoir being adapted to contain a fluid containing a beneficial agent therewithin;
   a catheter for delivering the fluid into a patient's body;
   a controllable pump, the pump communicating with the resevoir and the catheter and causing the fluid to move from the reservoir into the catheter upon receiving a command actuating same;
   a valve assembly comprising a deflectable energy storing member; and
   an electrical circuit configured to controllably energize and deflect the energy storing member by providing an output voltage and electric charge thereacross or therein, and configured to recover at least a portion of the electric charge from the deflectable energy storing member when the output voltage provided thereto is switched off.

2. The implantable medical device of claim 1, wherein the electrical circuit operably coupled to upper and lower surfaces of the deflectable energy storing member.

3. The implantable medical device of claim 1, wherein the energy storing member is deflectable or moveable between a first non-energized position in which movement of the fluid from the reservoir into the means for delivering the fluid into the patient's body is blocked, and a second energized position in which the movement of the fluid from the reservoir into the means for delivering the fluid into the patient's body is permitted.

4. The implantable medical device claim 1, wherein the energy storing member pushes or pulls a seal between a first sealed position in which movement of the fluid from the reservoir into the means for delivering the fluid into the patient's body is blocked, and a second unsealed position in which the movement of the fluid from the reservoir into the means for delivering the fluid into the patient's body is permitted, when the member is de-actuated and actuated, respectively.

5. The implantable medical device of claim 1, wherein the deflectable energy storing member comprises a piezo-electic material.

6. The implantable medical device of claim 1, wherein the deflectable energy storing member comprises a electro capacitive material.

7. The implantable medical device of claim 1, wherein the deflectable energy storing member comprises a electrostatic material.

8. The implantable medical device of claim 1, wherein the deflectable energy storing member comprises a solenoid.

9. The implantable medical device of claim 1, wherein the fluid reservoir further comprises means for maintaining the fluid containing a beneficial agent between a first pressure and second pressure.

10. The implantable medical device of claim 1, wherein the circuit comprises an integrated circuit comprising a driving circuit that receives electrical current from a power source and transforms the current into an output signal appropriate to cause the energy storing member to deflect in response to the application of an electrical field thereto such that a sealing means moves into an open position to permit fluid to flow from the fluid reservoir.

11. The implatnable medical device of claim 10, wherein the output signal ranges between about +80 Volts and about +150 Volts.

12. The implantable medical device of claim 1, wherein the means for controllably energizing and deflecting the deflectable energy storing member and the means for recovering electric charge from the energy storing member are coupled to a suitable power source.

13. The implantable medical device of claim 12, wherein the power source is selected from the group consisting of an electrochemical cell, a battery, a plurality of electrochemical cells, a storage capacitor, a super-capacitor and a electrolytic capacitor.

14. A method of causing fluid flow through an implantable beneficial agent infusion device, the device comprising a deflectable energy storing member and a fluid flow path blocked by the deflectable energy storing member in an un-energized position, the method comprising;
   (a) energizing the deflectable energy storing member with at least one of electric charge and electric voltage and causing same to deflect from an un-energized position to an energized position;
   (b) causing fluid to flow through the path blocked by the deflectable energy storing member in the un-energized position in response to the energy storing member deflecting;
   (c) de-energizing the deflectable energy storing member and causing same to move to the un-energized position, and
   (d) recovering at least a portion of the electric charge from the deflectable energy storing member when the deflectable energy storing member returns to its un-energized position.

15. The method of claim 14, wherein recovering at least a portion of the electric charge from the deflectable energy storing member comprises discharging a voltage through an inductor.

* * * * *

UNITED STATES PATENT AND TRADEMARK OFFICE
CERTIFICATE OF CORRECTION

PATENT NO. : 7,070,577 B1
APPLICATION NO. : 09/519563
DATED : July 4, 2006
INVENTOR(S) : Markus Haller and Koen J. Weijand It is certified that error appears in the above-identified patent and that said Letters Patent is hereby corrected as shown below:

Col. 11, Line 20: "resevoir" should read --reservoir--

Signed and Sealed this

Fifth Day of December, 2006

JON W. DUDAS
*Director of the United States Patent and Trademark Office*